(12) United States Patent
Niu et al.

(10) Patent No.: US 11,980,681 B2
(45) Date of Patent: May 14, 2024

(54) MATERIAL FOR DEMINERALIZING DENTIN COLLAGEN FIBRIL, PREPARATION METHOD AND APPLICATION THEREOF

(71) Applicant: THE FOURTH MILITARY MEDICAL UNIVERSITY OF CHINESE PEOPLE'S LIBERATION ARMY, Xi'an (CN)

(72) Inventors: Lina Niu, Xi'an (CN); Jihua Chen, Xi'an (CN); Zhiming Zheng, Xi'an (CN); Jingmei Guo, Xi'an (CN); Fan Yu, Xi'an (CN); Kai Jiao, Xi'an (CN)

(73) Assignee: The Fourth Military Medical University of Chinese People's Liberation Army, Xi'an (CN)

( * ) Notice: Subject to any disclaimer, the term of this patent is extended or adjusted under 35 U.S.C. 154(b) by 0 days.

(21) Appl. No.: 17/744,275

(22) Filed: May 13, 2022

(65) Prior Publication Data
US 2022/0273546 A1 Sep. 1, 2022

Related U.S. Application Data

(62) Division of application No. 16/791,343, filed on Feb. 14, 2020, now abandoned.

(30) Foreign Application Priority Data

Apr. 16, 2019 (CN) .......................... 201910302362.9

(51) Int. Cl.
*A61K 8/73* (2006.01)
*A61K 6/20* (2020.01)

(52) U.S. Cl.
CPC .............. *A61K 8/736* (2013.01); *A61K 6/20* (2020.01)

(58) Field of Classification Search
CPC .................................. A61K 8/736; A61K 6/20
See application file for complete search history.

(56) References Cited

U.S. PATENT DOCUMENTS 6,689,343 B1 2/2004 Allred
9,949,644 B2 4/2018 Li et al.

2003/0157034 A1 8/2003 Jia et al.
2011/0076646 A1 3/2011 Kanca, III
2012/0161067 A1 6/2012 Lee et al.

FOREIGN PATENT DOCUMENTS

CN 102068318 A * 5/2011
WO WO-2011028968 A1 * 3/2011 ............. A61K 8/736

OTHER PUBLICATIONS

CN-102068318-A Translation, May 2011 (Year: 2011).*
Elsevier; Acta Biomaterialia 90 (2019) 424-440; Guo, Jing-Mei et al.; "Polymer Conjugation Optimizes EDTA as a Calcium-Chelating Agent That Exclusively Removes Extrafibrillar Minerals From Mineralized Collagen".
Bernkop-Schnurch et al. (Pharmaceutical research, vol. 14 No. 7, 1997); (Year:1997).
Gu et al. (Journal of Dental research, 2019, vol. 98 92) 186-193). (Year:2019).
Valenta et al. (J. Pharm. Pharmacol. 1998, 50: 445-452); (Year 1998).
IN 201741020217 (Year: 2018).
Synthesis Characterization by Feng et al. (Molecules 2017,22,1253) (Year 2017).

* cited by examiner

*Primary Examiner* — Snigdha Maewall
(74) *Attorney, Agent, or Firm* — DeLio Peterson & Curcio LLC; Kelly M Nowak

(57) ABSTRACT

The invention relates to a dentin collagen fibril demineralizing material, and a preparation method and application thereof. The invention relates to a conjugate of water-soluble chitosan and an aminocarboxylic acid metal chelating agent used for dental demineralization, preferably dentin demineralization. The invention also discloses a dentin collagen fibril demineralizing material and a preparation method and application thereof, wherein the material is prepared from 0.5-1 part by mass of water-soluble chitosan, 10-30 parts by mass of EDTA, and 0.8-1.5 parts by mass of cross-linking agent. The invention relates to a dental demineralization composition comprising a conjugate and a material of the invention. The conjugate, material and composition can be used for dentin demineralization treatment before dental bonding and restoration. When used as a dentin collagen demineralizing agent, they have excellent selective extrafibrillar demineralization performance, good biological compatibility, effective anti-bacterial activity, endogenous matrix protease-inhibiting activity and extremely low cytotoxicity.

19 Claims, 3 Drawing Sheets

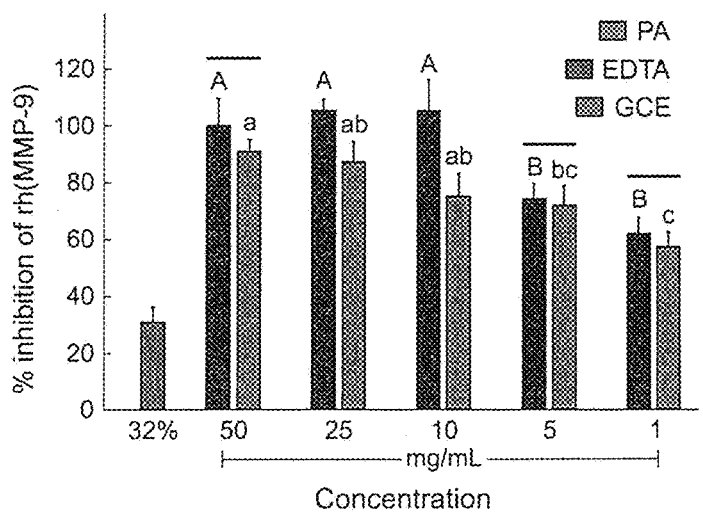
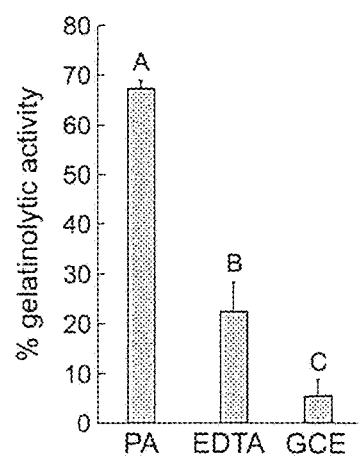
Fig. 4A
Fig. 4B
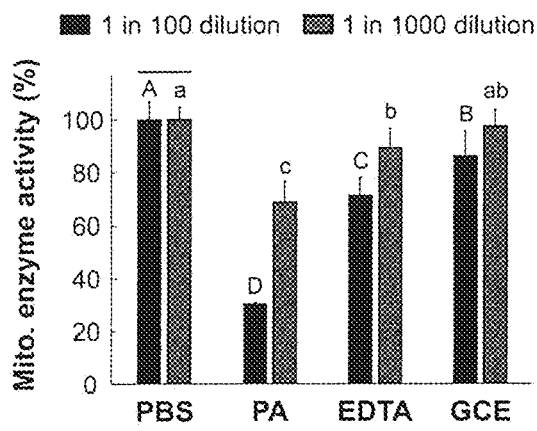
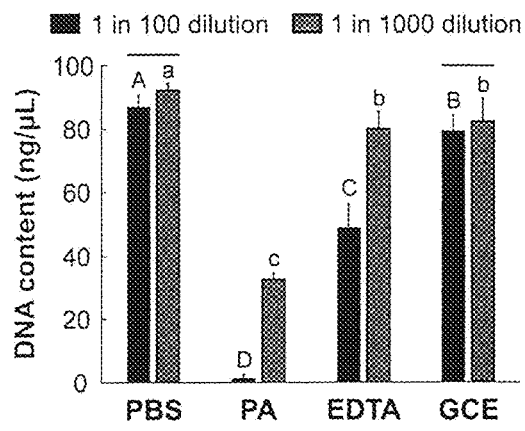
Fig. 5A
Fig. 5B

MATERIAL FOR DEMINERALIZING DENTIN COLLAGEN FIBRIL, PREPARATION METHOD AND APPLICATION THEREOF

BACKGROUND OF THE INVENTION

1. Field of the Invention

The invention belongs to the field of dental bonding and restorative material, and particularly relates to a material for demineralizing dentin collagen fibril and a preparation method and application thereof.

2. Description of Related Art

Teeth are highly mineralized organs of the human body. The normal dentin matrix consists of an orderly woven collagen fibril matrix, an orderly arrangement of inorganic phase apatite crystals, and a small amount of non-collagenous protein.

According to the relative positional relationship between hydroxyapatite and collagen, the mineralization of dentin can be divided into two parts: intrafibrillar mineralization and extrafibrillar mineralization. Although 65% of the minerals in dentin are located outside the fibrils, intrafibrillar mineralization is essential to maintain the fibril morphology, and determines the mechanical properties of dentin on the nanoscale, and can prevent denatured degradation of collagen by exogenous matrix metalloproteinases in the dentin.

Under normal physiological conditions, the demineralization and remineralization of the teeth are balanced. However, under pathological conditions, the demineralization effect will be greater than the remineralization effect, leading to the destruction of dental tissues, which in turn will damage the function of the teeth.

Oral caries, the most common oral disease, is the result of the most common pathological demineralization. Cariogenic microorganisms can decompose carbohydrates to produce acid, and synergize with endogenous matrix metalloproteinases of dentin, leading to the demineralization of dental minerals and the degradation of collagen organic substances, and gradually form cavities. At present, caries has been listed by the World Health Organization as the third largest non-communicable disease after cancer and cardiovascular disease. According to the World Health Organization (WHO) research data in 2015, 2.4 billion people have caries in permanent teeth and 621 million people have caries in deciduous teeth. The prevention and treatment of caries is not only an issue of stomatology, but it has also become a public health concerning topic.

At present, the clinical treatment of dental caries is still based on surgical treatment. Namely, on the basis of removing the dental caries, firstly, the bonding surface is etched with an acid etchant (such as 30-40% phosphoric acid) so that the dentin collagen fibrils are demineralized; then a binder is applied in and cross-linked with the exposed collagen fibrils to form a mixed layer; finally, the cavity is filled with restorative materials to restore the physiological form and function of the teeth. The restorative materials used are mainly tooth-color composite resin materials based on resin dentin bonding. It can be seen that the integrity and stability of the mixed layer formed by the bonding agent and dentin collagen are key factors in the success of the treatment and the long-term existence of the restoration. However, due to the strong acid etching of phosphoric acid, the dentin collagen matrix is often completely under the action of an acid etchant. After drying, the dendritic collagen matrix collapses into a sheet shape, making it difficult for the resin adhesive to penetrate into the collagen fibrils. As a result, collagen cannot be well protected by the bonding resin. Under the action of endogenous matrix protease, this part of the poorly penetrated resin area is easily degraded, so that the integrity of the bonding surface is damaged, and the bonding strength is reduced, which may eventually lead to the failure of the resin-dentin bonding restoration. In addition, some studies have found that these endogenous matrix proteases can be activated in a large amount in an acidic environment. Therefore, the use of phosphoric acid to etch dentin stimulates the activity of matrix proteases to a certain extent. These shortcomings are the main factors causing secondary caries around the restoration and degradation of dentin collagen.

Chitin is a homopolysaccharide with the structure of N-acetylglucosamine polymerized through beta linking. It is widely found in the shells of crustaceans, the crusts of insects, and the cell walls of fungi. The chemical name of chitosan is $\beta$-(1→4)-2-amino-2-deoxy-D-glucose, which is the product of N-deacetylated chitin. Generally, for the chitosan, N-acetyl groups are removed more than 55%.

The chelating agent can interact with metal atom or ion, and enclose the metal atom or ion within the chelating agent to form a stable complex or chelate.

SUMMARY OF THE INVENTION

Bearing in mind the problems and deficiencies of the prior art, it is therefore an object of the present invention to provide a dental demineralizing agent, which can prevent and treat dental caries and improve the stability of the bonding interface, thereby prolonging the service life of the bonding restoration. More specifically, it is an object of the present invention to provide a conjugate, material and composition for use in dental demineralization, more specifically demineralization of dentin collagen fibril. For example, the object of the present invention is to provide a material for demineralizing dentin collagen fibril. The conjugate, material, and composition can maintain the original appearance and network structure of dentin collagen fibrils and facilitate subsequent penetration of the resin binder. It is also an object of the present invention to provide methods of dental bonding restoration using the conjugate, material and composition of the invention.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIG. 4A shows that EDTA and glycol chitosan-EDTA have similar inhibitory effects on the activity of endogenous recombinant human matrix metalloproteinase-9.

FIG. 4B compares degree of degradation of dentin collagen in each group of the dentin mixed layers.

FIG. 5A detects the mitochondrial dehydrogenase activity (Mito.) of human dental pulp stem cells (hDPSCs) that had been exposed to different dentin demineralizing agents.

FIG. 5B detects intracellular DNA content of human dental pulp stem cells that had been exposed to different dentin demineralizing agents.

DESCRIPTION OF THE EMBODIMENT(S)

Figure 1:
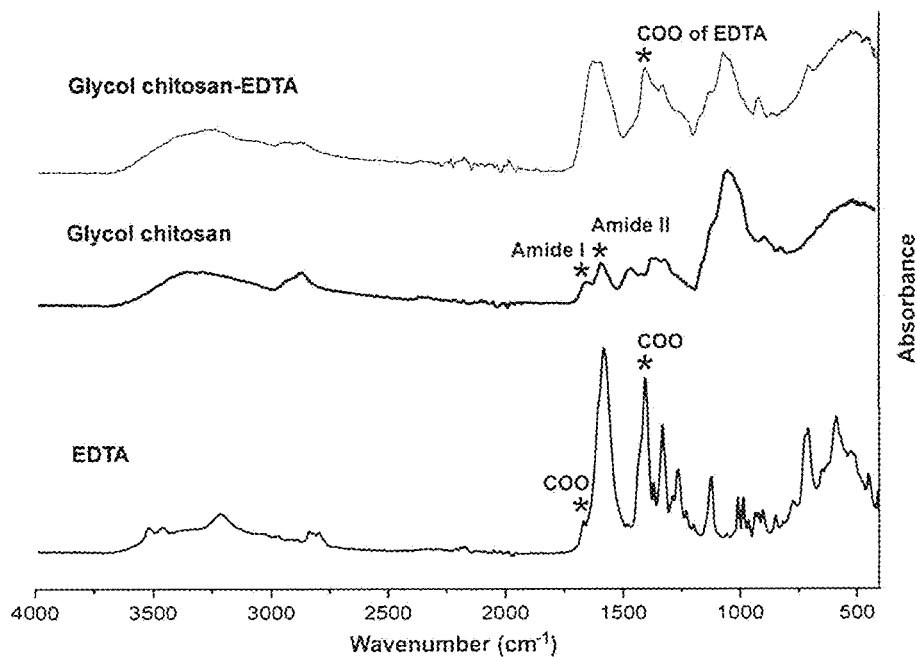
FIG. 1 shows the infrared spectra of EDTA, glycol chitosan and EDTA-crosslinked glycol chitosan.

In describing the embodiment of the present invention, reference will be made herein to FIGS. 1-5B of the drawings in which like numerals refer to like features of the invention.

The present invention provides a dental demineralizing agent, which can prevent and treat dental caries and improve the stability of the bonding interface, thereby prolonging the service life of the bonding restoration. More specifically, it is an object of the present invention to provide a conjugate, material and composition for use in dental demineralization, more specifically demineralization of dentin collagen fibril. For example, the object of the present invention is to provide a material for demineralizing dentin collagen fibril. The conjugate, material, and composition can maintain the original appearance and network structure of dentin collagen fibrils and facilitate subsequent penetration of the resin binder.

The technical problem of the present invention is solved by providing a conjugate of water-soluble chitosan and an aminocarboxylic acid metal chelating agent.

In one aspect, the invention relates to a conjugate of a water-soluble chitosan and an aminocarboxylic acid metal chelating agent for use in dental demineralization, preferably dentin demineralization, more preferably demineralization of dentin collagen fibril. In the conjugate, the amino group of the water-soluble chitosan and the carboxyl group of the aminocarboxylic acid metal chelating agent form an amide bond.

In the present invention, chitosan can have the following structural formula:

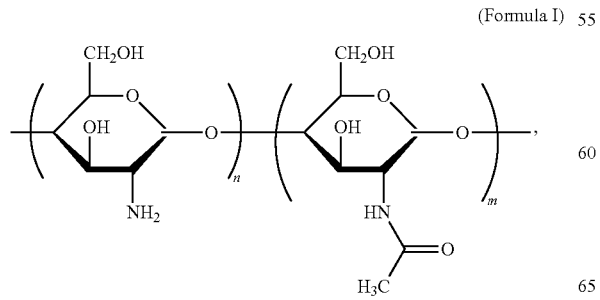

(Formula I)

where n and m are integers and the ratio of n to m depends on the degree of deacetylation of the chitosan. In one aspect, the degree of deacetylation of the chitosan of the present invention is at least 55%, such as 60% to 100%, 65% to 99%, 70% to 98%, 75% to 97%, 80% to 96%, 85% to 95%, or at least 90%. For example, for chitosan with a degree of deacetylation of 90%, in the above structural formula, the ratio of n to m is 9:1. Those skilled in the art understand that in the above formula (I), the amino-containing monomer (i.e., glucosamine monomer) and the acetamido-containing monomer (i.e., acetylglucosamine monomer) are generally randomly distributed, including that the position of the monomers and the consecutive number of identical monomers can be random. In one aspect, the total number of n+m is greater than 100, such as greater than 150, preferably greater than 200, greater than 250, greater than 300, greater than 350, greater than 400, greater than 450, greater than 500, greater than 600, greater than 800, or greater than 1000. In another aspect, the total number of n+m is less than 10,000, preferably less than 8,000, less than 7,000, less than 6,000, less than 5,000, less than 4,000, less than 3,500, less than 3,000, less than 2,500, less than 2,000, or less than 1,500.

In the present invention, chitosan can have the following structural formula:

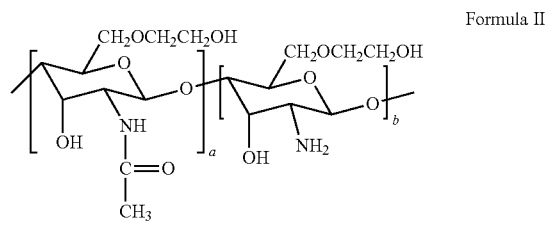

Formula II where n and m are integers and the ratio of n to m depends on the degree of deacetylation of the chitosan. In one aspect, the degree of deacetylation of the chitosan of the present invention is at least 55%, such as 60% to 100%, 65% to 99%, 70% to 98%, 75% to 97%, 80% to 96%, 85% to 95%, or at least 90%. For example, for chitosan with a degree of deacetylation of 90%, in the above structural formula, the ratio of n to m is 9:1. Those skilled in the art understand that in the above formula (I), the amino-containing monomer (i.e., glucosamine monomer) and the acetamido-containing monomer (i.e., acetylglucosamine monomer) are generally randomly distributed, including that the position of the monomers and the consecutive number of identical monomers can be random. In one aspect, the total number of n+m is greater than 100, such as greater than 150, preferably greater than 200, greater than 250, greater than 300, greater than 350, greater than 400, greater than 450, greater than 500, greater than 600, greater than 800, or greater than 1000. In another aspect, the total number of n+m is less than 10,000, preferably less than 8,000, less than 7,000, less than 6,000, less than 5,000, less than 4,000, less than 3,500, less than 3,000, less than 2,500, less than 2,000, or less than 1,500.

In one aspect, the aminocarboxylic acid metal chelating agent of the present invention has a carboxyl group capable of forming an amide bond with an amino group of a water-soluble chitosan. In addition, the chelating agent is usually a polybasic carboxylic acid (e.g., a 1 to 6 basic carboxylic acid) containing one or more amino groups (e.g., 1 to 4 amino groups, usually tertiary amino groups), where the amino and carboxyl groups are capable of interacting with a metal atom/ion to form coordination bonds. In addition, the chelating agent can have 6 to 18 carbon atoms, such as 6, 10, 14, 16, or 18 carbon atoms, and optionally have a hydroxyl group and/or an oxy group. In one aspect, the metal atom or ion that the aminocarboxylic acid metal chelating agent can chelate includes calcium, magnesium, iron, copper, zinc, and the like, preferably calcium. Examples of aminocarboxylic acid metal chelating agents include ethylenediaminetetraacetic acid (EDTA), hydroxyethyl ethylenediaminetriacetic acid (HEDTA), diethylenetriaminepentaacetic acid (DTPA), aminotriacetic acid (also known as nitrilotriacetic acid, NTA), dihydroxyethyl glycine (DEG), ethylene glycol tetraacetic acid (EGTA), ethylenediamine diacetic acid (EDDHA), triethylenetetraaminehexaacetic acid (TTHA), cyclohexanediamine tetraacetic acid (CDTA), 1,4,7,10-tetraazacyclododecane-1,4,7,10-tetraacetic acid (DOTA), 1,4,8,11-tetraazacyclododecane-1,4,8,11-tetraacetic acid (TETA), preferably ethylenediaminetetraacetic acid. In one aspect, the aminocarboxylic acid metal chelating agent may include the above polybasic carboxylic acid or a salt thereof, such as a sodium or potassium salt.

In one aspect, the invention relates to a dental demineralizing material, preferably a material for demineralizing dentin collagen fibril. In this aspect, the dental demineralizing material is made by a conjugation reaction between the water-soluble chitosan and the aminocarboxylic acid metal chelating agent. In this aspect, the conjugation reaction is performed in the presence of a cross-linking agent. In the reaction, relative to the total mass of the reactants, the part by mass of water-soluble chitosan can be 0.05 to 20, preferably 0.1 to 15, 0.2 to 10, 0.5 to 8, such as 0.8, 0.9, 1, 1.2, 1.5, 2, 3, 4 or 5. In the reaction, relative to the total mass of the reactants, the part by mass of the aminocarboxylic acid metal chelating agent can be 1 to 60, preferably 5 to 50, 10 to 40, such as 15, 20, 25, 30, 35, or 45. In the reaction, relative to the total mass of the reactants, the part by mass of the cross-linking agent can be 0.1 to 15, preferably 0.2 to 10, 0.5 to 5, such as 0.6, 0.8, 1, 1.5, 2, 2.5, 3, or 3.5.

Preferably, the material provided by the present invention is prepared from 0.5-1 part by mass of water-soluble chitosan, 10-30 parts by mass of aminocarboxylic acid metal chelating agent, and 0.8-1.5 parts by mass of cross-linking agent.

The material provided by the present invention is prepared from 0.5-1 part by mass of water-soluble chitosan, 10-30 parts by mass of EDTA, and 0.8-1.5 parts by mass of a cross-linking agent. Covalent binding reaction between water-soluble chitosan and EDTA is conducted through the action of the cross-linking agent.

In the above-mentioned conjugation reaction or covalent bonding reaction, an amide bond is formed between the free amine group of the water-soluble chitosan and the free carboxyl group of the aminocarboxylic acid metal chelating agent.

Preferably, the pH of the material according to the invention is neutral or alkaline.

Preferably, the water-soluble chitosan of the present invention is selected from the group consisting of glycol chitosan, carboxymethyl chitosan, chitosan hydrochloride, chitosan quaternary ammonium salt, chitosan sulfate ester, chitosan oligosaccharide, or hyaluronic acid-like chitosan or the mixture thereof.

Preferably, the cross-linking agent of the present invention is selected from 1-ethyl-3-(3-dimethylaminopropyl)-carbodiimide, N-hydroxysuccinimide, glutaraldehyde, bisimidate ester, or maleimide, or a mixture thereof.

In one aspect, the content of free amino group of the conjugate or material of the present invention is less than 20%, preferably 0% to 15%, such as 0.5% to 10%, such as 1% to 5%, such as about 1.5%, about 2%, about 2.5%, about 3%, about 3.5%, about 4%, or about 4.5%, as compared to the water-soluble chitosan prior to the conjugation reaction or covalent binding reaction.

In one aspect, the conjugate and material of the invention has a Mn of greater than 40 kDa, preferably greater than 50 kDa, such as 60 kDa to 600 kDa, 80 kDa to 500 kDa, 100 kDa to 400 kDa, 120 kDa to 300 kDa, 150 kDa to 200 kDa, for example about 130 kDa, about 140 kDa, about 160 kDa, about 170 kDa, about 180 kDa, or about 190 kDa.

In one aspect, the conjugate and material of the invention has a Mw of greater than 80 kDa, preferably greater than 100 kDa, such as 200 kDa to 800 kDa, such as 300 kDa to 700 kDa, such as about 250 kDa, about 350 kDa, about 400 kDa, about 450 kDa, about 500 kDa, about 550 kDa, about 600 kDa, or about 650 kDa.

In one aspect, the conjugate and material of the invention has a Mp of greater than 60 kDa, preferably greater than 70 kDa, such as 80 kDa to 600 kDa, such as 100 kDa to 500 kDa, such as about 150 kDa, about 200 kDa, about 250 kDa, about 300 kDa, about 350 kDa, about 400 kDa, or about 450 kDa.

In one aspect, the polydispersity index PDI of the conjugate and material of the present invention is 1 to 5, preferably 2 to 4, such as about 1.5, about 2.5, about 3, about 3.5, or about 4.5.

In one aspect, the conjugate or material of the invention has a neutral or basic pH, such as pH 7-10, such as 7.5, 8, 8.5, 9 or 9.5.

In one aspect, the invention relates to a conjugate of glycol chitosan and ethylenediaminetetraacetic acid or a dental demineralizing material made from the conjugate. In one aspect, the conjugate and material can be represented by the following structural formula:

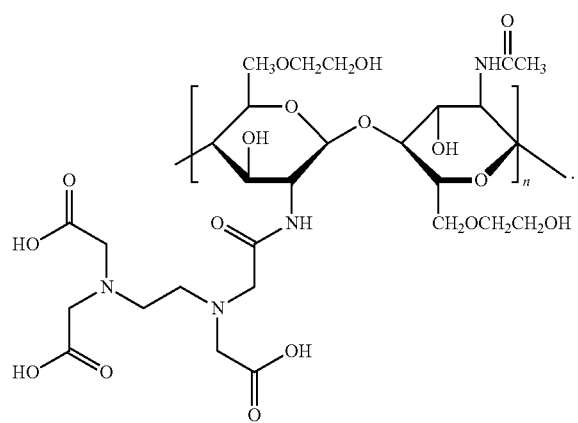

FIG. III

Those skilled in the art understand that the conjugate having Formula III may also include a monomer (i.e., glucosamine monomer) containing a free amino group that do not form an amide bond with a carboxyl group of EDTA. In addition, those skilled in the art understand that in the conjugate, the acetamide group-containing monomer (i.e., an acetylglucosamine monomer), the EDTA amide group-containing monomer (i.e., an EDTA acylated glucosamine monomer) and the optional free amino-containing monomer (i.e., glucosamine monomer) are generally randomly distributed in Formula III, including that the position of the monomers and the continuous number of identical monomers can be random. In the conjugate or material or formula III, the ratio between the EDTA amide group-containing monomers (optionally together with the free amino group-containing monomers) and the acetamide group-containing monomers is variable, depending on the degree of deacetylation of the glycol chitosan which degree is defined above with respect to Formula I or Formula II. In the conjugate or material, the content of free amine group of the conjugate or material according to the present invention is less than 20%, preferably 0% to 15%, such as 0.5% to 10%, such as 1% to 5%, such as about 1.5%, about 2%, about 2.5%, about 3%, about 3.5%, about 4%, or about 4.5%, as compared with the glycol chitosan prior to the conjugation reaction or covalent binding reaction. In one aspect, n is greater than 100, such as greater than 150, preferably greater than 200, greater than 250, greater than 300, greater than 350, greater than 400, greater than 450, greater than 500, greater than 600, greater than 800, or greater than 1000. In another aspect, n is less than 10,000, preferably less than 8,000, less than 7,000, less than 6,000, less than 5,000, less than 4,000, less than 3,500, less than 3,000, less than 2,500, less than 2,000, or less than 1,500.

In one aspect, the invention relates to a dental demineralizing composition comprising the conjugate or material of the present invention, and an orally acceptable excipient or vehicle. In the composition, based on the weight of the composition, the content of the conjugate or material is 0.05% to 50% by weight, preferably 0.1% to 40% by weight, such as 0.2% to 30% by weight, 0.5% to 20% by weight, 1% to 10% by weight, such as 1.5%, 2%, 2.5%, 3%, 3.5%, 4%, 4.5%, 5%, 5.5%, 6%, 7%, 8%, or 9% by weight. In this aspect, the conjugate material according to the present invention can be in the form of a powder (e.g., a lyophilized powder), a solution, a gel, or a suspension. In the dental demineralizing composition of the present invention, the orally acceptable excipient or vehicle refers to the excipient or vehicle that is provided in a concentration or amount that is safe for the human body when applied to the oral cavity and does not generally interfer with the activity of another active ingredient in the composition. In one example, the excipient includes a gelling agent, a thickening agent, a surfactant, a dye, or a preservative, etc., as described in US Patent Publication Nos. US2003/0157034A1, US2011/0076646A1, and US2012/0161067A1, which are incorporated herein by reference. In one example, the vehicle may include water.

In one aspect, the invention relates to a dental bonding and restorative kit comprising a conjugate, material or composition according to the invention, and a dental bonding agent and/or restorative agent. Examples of the bonding agent and restorative agent include dental silver alloy powder; composite resins such as acrylic resins; cements and the like. For example, the bonding agent and/or restorative agent are those commercially available under the trade names Adper™ Single Bond 2 or Filtek™ Z250.

In one aspect, the present invention relates to a method of dental bonding restoration, the method comprising (a) applying an effective amount of a conjugate, material or composition of the invention to a tooth surface in need of restoration, optionally removing said conjugate, material, or composition; and applying the dental bonding agent and/or restorative agent to the tooth surface in need of restoration.

In one aspect, the present invention relates to a method for preparing a conjugate, material or composition of the present invention, the method comprising: mixing a water-soluble chitosan with an aminocarboxylic acid metal chelating agent in the presence of a cross-linking agent to obtain a conjugate of the water-soluble chitosan with the aminocarboxylic acid metal chelating agent. Preferably, the conjugate is prepared by mixing 0.5-1 part by mass of water-soluble chitosan, 10-30 parts by mass of aminocarboxylic acid metal chelating agent, and 0.8-1.5 parts by mass of cross-linking agent.

The invention also provides a method for preparing material for demineralizing dentin collagen fibril.

The method provided by the present invention includes the steps of mixing the aqueous water-soluble chitosan solution with the EDTA aqueous solution, dissolving the cross-linking agent in the mixed solution, and performing the reaction at room temperature. In the presence of the cross-linking agent, a covalently binding action occurs between the water-soluble chitosan and EDTA. In the reaction, relative to the total mass of the reactants, the part by mass of the water-soluble chitosan can be 0.05 to 20, preferably 0.1 to 15, 0.2 to 10, 0.5 to 8, such as 0.8, 0.9, 1, 1.2, 1.5, 2, 3, 4 or 5. In the reaction, relative to the total mass of the reactants, the part by mass of the aminocarboxylic acid metal chelating agent can be 1 to 60, preferably 5 to 50, 10 to 40, such as 15, 20, 25, 30, 35, or 45. In the reaction, relative to the total mass of the reactants, the part by mass of the cross-linking agent can be 0.1 to 15, preferably 0.2 to 10, 0.5 to 5, such as 0.6, 0.8, 1, 1.5, 2, 2.5, 3, or 3.5.

Preferably, in the preparation method of the present invention, the pH of the mixed solution is adjusted to be neutral or alkaline, such as pH 7-10, such as 7.5, 8, 8.5, 9 or 9.5.

Preferably, the method of the present invention includes the steps of mixing an aqueous water-soluble chitosan solution at a concentration of 5 to 10 mg/ml with an aqueous EDTA solution at a concentration of 100 to 300 mg/ml in an equal volume; adjusting the pH of the mixed solution to pH 6.0; and afterwards adding 8 to 15 mg of a cross-linking agent at room temperature for 12-16 hours; removing the unreacted residue by dialysis under an appropriate condition; and freeze-drying to obtain a material for demineralizing dentin collagen fibril.

The material for demineralizing dentin collagen fibril of the present invention can be used for dentin demineralizing treatment in dental bonding restoration, and used for preparing dental bonding and restorative system.

The invention has the following effects.

In the present invention, most of the donor atoms in the molecular structure of the aminocarboxylic acid metal chelating agent (such as EDTA) are bonded to the skeleton of the optimized water-soluble chitosan through covalent cross-linking, thereby preparing a new type of calcium ion chelating agent, which make full use of the natural macromolecular properties of chitosan and the excellent calcium ion chelating ability of EDTA. This can exert multiple advantages when the conjugate or material according to the present invention is applied to the mineralized dentin surface in the carious area.

First, the water-soluble chitosan covalently bonded with an aminocarboxylic acid metal chelating agent (such as EDTA) has a significantly enhanced ability to chelate calcium ion, quickly reacts with minerals outside of dentin collagen fibrils, and completes demineralization within the time frame (30 seconds or less) which is acceptable in clinical treatment.

Second, the natural dentin collagen itself has selective permeability. Materials with a molecular weight greater than 40 kDa will be completely excluded from the collagen molecules. Materials with a molecular weight less than 6 kDa can freely pass through the space within the collagen fibrils. Materials with molecular weight between 6 kDa and 40 kDa partially access to the inner of collagen fibrils. Due to the large molecular weight of water-soluble chitosan (82 kDa), the chelating agent cannot enter the inside of the fibril, so that it selectively removes the extrafibrillar minerals from the dentin collagen at the bonding interface and retains the intrafibrillar minerals. This maintains network structure of dentin collagen and promotes the penetration of adhesive resin.

Third, the water-soluble chitosan is rich in polycationic structures, which can significantly inhibit planktonic microorganisms and bacterial bio-membranes in secondary caries and active root surface caries and allow this new type of calcium ion chelating agent to have the dual functions of rapid demineralization and effective antibacterial action.

Fourth, the excellent biocompatibility and low cytotoxicity of the water-soluble chitosan can effectively protect the activity of dental pulp stem cells in a living pulp tooth, avoid the adverse stimulating effect of traditional acid etchants on dental pulp stem cells and provide good prerequisites for regeneration of caries-affected and demineralized dentin.

Fifth, the covalent conjugate of water-soluble chitosan and aminocarboxylic acid metal chelating agent (such as EDTA) is neutral or alkaline in PH, which avoids the local acid environment formed by traditional acid etching agents and causes deficiency or insufficiency of activation of endogenous matrix proteases. Meanwhile, due to the chelation of a large amount of calcium ions during the demineralization process, the activity of matrix proteases around the mixed layer of dentin collagen was significantly inhibited, thereby protecting the collagen from enzymatic degradation.

In summary, the present invention can selectively remove the extrafibrillar minerals from dentin collagen, so that the dentin collagen fibrils maintain their original morphology and network structure, which is beneficial to the subsequent resin adhesive penetration. Meanwhile, the inner of collagen can be still protected by minerals from degradation under exogenous stimulation. It achieves obvious effects on preventing dental caries, improving the stability of the bonding interface, and extending the use of bonding restorations.

EXAMPLES

The invention comprehensively utilizes the advantages of water-soluble chitosan as a natural macromolecule and the efficient calcium ion chelation of EDTA. The method according to present invention comprises mixing a water-soluble chitosan solution and an aqueous EDTA solution in an equal volume, and adding a covalent cross-linking agent to conduct a covalent bonding reaction under the action of the cross-linking agent.

The following are specific Examples provided by the inventor to further explain and elaborate the technical solution of the present invention.

Example 1

The material used in this Example was prepared as follow: mixing an aqueous solution of glycol chitosan (degree of polymerization ≥400, MilliporeSigma, St.Louis, MO, USA) with an aqueous solution of EDTA at an appropriate concentration, adding 1-ethyl-3-(3-dimethylaminopropyl)-carbodiimide cross-linking agent and continuously stirring for 14 hours at room temperature, and removing the unreacted residue by using an appropriate dialysis condition. The total amount used was glycol chitosan 10 g, EDTA 300 g, and 1-ethyl-3-(3-dimethylaminopropyl)-carbodiimide cross-linking agent 15 g.

For example, a preferred dialysis condition was to place the above reaction solution in a dialysis membrane with a cut-off molecular weight of 12-14 kDa and containing 0.05 M NaOH to remove reactants with smaller molecular weight. The uncrosslinked residues were removed via dialysis by using dialysis membrane with a cut-off molecular weight of 12-14 kDa and containing double distilled water. The total amount used was glycol chitosan 10 mg, EDTA 300 mg, and 1-ethyl-3-(3-dimethylaminopropyl)-carbodiimide cross-linking agent 15 mg. During the process, the EDTA can be sufficiently and rapidly dissolved by adjusting the pH value, for example, adjusting the pH to 8.0.

In a preferred embodiment, a neutral or alkaline demineralizing material can be prepared by adjusting the pH of the mixed solution to be neutral or alkaline during preparation.

Example 2

This Example was different from Example 1 in:
(1) dissolving glycol chitosan in deionized water to form a chitosan solution at a concentration of 10 mg/ml;
(2) dissolving EDTA in deionized water to form an aqueous EDTA solution at a concentration of 300 mg/ml;
(3) mixing the above two solutions in an equal volume and adjusting the pH of the mixed solution to 6.0;
(4) dissolving the 1-ethyl-3-(3-dimethylaminopropyl)-carbodiimide cross-linking agent in the above mixed solution at a concentration of 15 mg/ml to allow the carboxyl functional group on the EDTA molecular chain to covalently bond to the amino functional group on the soluble chitosan skeleton, meanwhile continuously stirring for 14 hours at room temperature; and
(5) dialyzing the above reaction solution by using a dialysis membrane with a cut-off molecular weight of 12-14 kDa and containing 0.05 M NaOH to remove reactants with smaller molecular weight, wherein the uncrosslinked residues were removed via dialysis by using dialysis membrane with a cut-off molecular weight of 12-14 kDa and containing double distilled water; and storing at −20° C. for lyophilization; so that a calcium ion chelator material of water-soluble EDTA cross-linked chitosan was provided.

According to Example 2, the calcium ion chelator material water-soluble EDTA-crosslinked chitosan constructed by the present invention had the characteristics as shown below.

FIG. 1 show the infrared spectrum of EDTA, glycol chitosan, and EDTA cross-linked glycol chitosan. The position and intensity of the infrared absorption peak reflected the features of the structure, composition and chemical groups of EDTA, glycol chitosan, and EDTA cross-linked glycol chitosan. For EDTA cross-linked glycol chitosan, characteristic absorption peaks (C=O stretching vibrations) of EDTA were detected at a wavelength of 1300-1400 $cm^{-1}$, indicating that chemical bonding between EDTA and glycol chitosan occurred.

Figure 2:
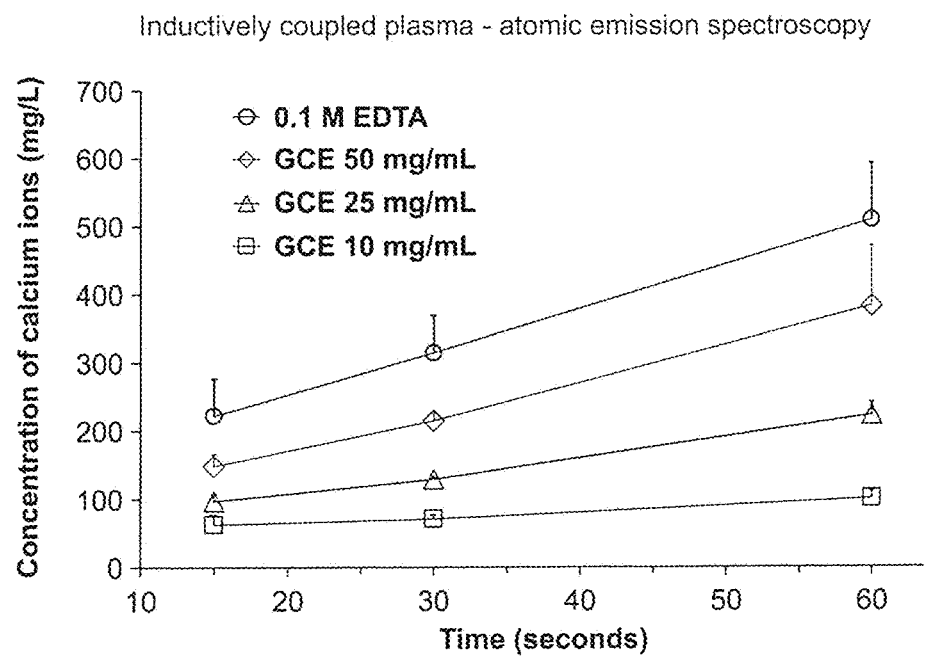
FIG. 2 shows in an inductively coupled plasma-atomic emission spectrometry method for measuring mineralized dentin, the rate of chelating $Ca^{2+}$ by the calcium chelator EDTA cross-linked glycol chitosan at different concentrations (50, 25, and 10 mg/ml) as compared with the control 0.1M EDTA.

FIG. 2 show in an inductively coupled plasma-atomic emission spectrometry method for measuring mineralized dentin, the rate of chelating $Ca^{2+}$ by the calcium chelator EDTA cross-linked glycol chitosan at different concentrations (50, 25, and 10 mg/ml) as compared with the control 0.1M EDTA. The results showed that 0.1M EDTA had the strongest demineralization effect. The demineralization ability of EDTA cross-linked glycol chitosan was improved, as the concentration thereof increased.

Figure 3A:
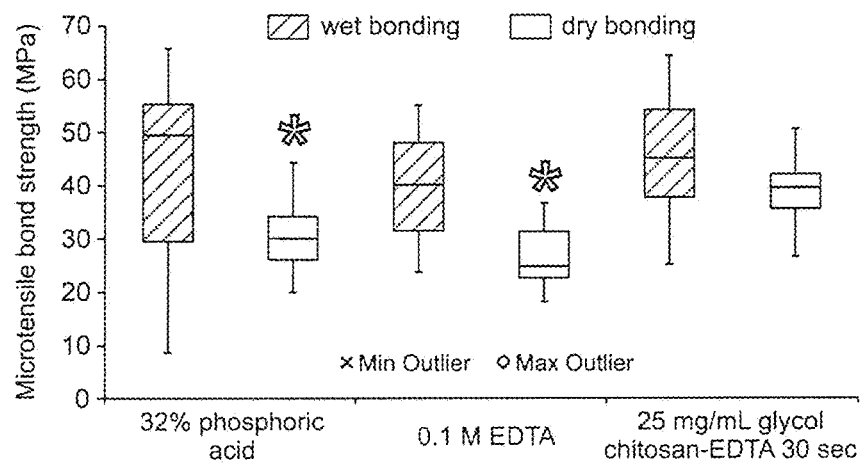
FIG. 3A shows comparison of the microtensile strength of dentin bonded with the bonding agent in the wet bonding or dry bonding mode by using different dentin demineralizing agents 32% phosphoric acid (PA), 0.1M EDTA, or 25 mg/ml EDTA cross-linked glycol chitosan (glycol chitosan-EDTA, GCE).
Figure 3B:
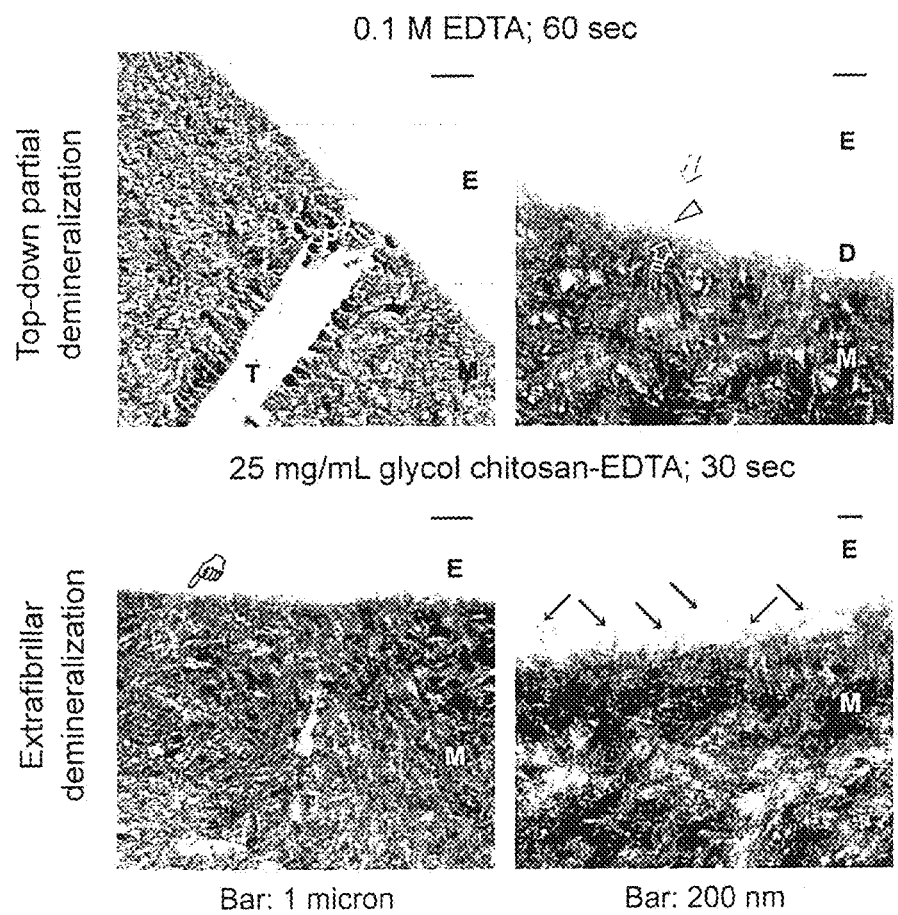
FIG. 3B is a transmission electron microscope image of mineralized dentin treated with different dentin demineralizing agents 0.1M EDTA or 25 mg/ml EDTA cross-linked glycol chitosan.

FIGS. 3A and 3B show the effects of different dentin demineralizing agents (phosphoric acid (PA), 0.1M EDTA, or 25 mg/ml EDTA cross-linked glycol chitosan (GCE)) on the bonding strength after the treatment to the dentin surface. For wet bonding, the conditioned specimen was kept moist by removing excess water from the dentin surface with lint-free tissues prior to bonding. For dry bonding, the conditioned dentin was air-dried with of land moisture-free air for 5 sec. The dentin bond strength was measured by the following methods. After treatment with various demineralizing agents and rinsing with deionized water, each tooth segment was bonded with Adper Single Bond 2 (3M ESPE; St Paul, MN, USA). After bonding, a 4-mm thick of resin composite (Z250, 3M ESPE) was placed over the adhesive-coated dentin surface using incremental light-curing. The bonded teeth with composite build-ups were stored in water for 24 hours at 37° C. Each specimen was subsequently sectioned to 0.9 mm×0.9 mm×7 mm long sticks, each with the resin-dentin interface in the middle of the stick. Each stick was attached with cyanoacrylate glue (Zapit; Dental Ventures of America, Corona, CA, USA) to a testing jig and stressed to failure under tension in a universal testing machine (Vitrodyne V1000; Liveco Inc., Burlington, VT, USA) at a cross-head speed of 1 mm/min. The tensile load at failure was recorded and divided by the measured cross-sectioned area of each beam to yield the tensile bond strength. The mean bond strength value derived from the 4 beams of each tooth was used to represent the tensile bond strength of that particular tooth. Data analysis was subsequently performed using the tooth as the statistical unit (n=10 teeth). FIG. 3A showed comparison of the microtensile strength of dentin bonded with the bonding agent in the wet bonding or dry bonding mode by using 32% phosphoric acid treatment for 15 seconds; 0.1M EDTA treatment for 60 seconds, or 25 mg/ml glycol chitosan-EDTA for 30 seconds. Statistical analysis was conducted by using phosphoric acid-wet bonding as a control group. The results showed that in the dry bonding mode, 32% phosphoric acid and 0.1M EDTA groups exhibited a significant decrease in bonding strength (p<0.05). The 25 mg/ml glycol chitosan-EDTA group in both dry bonding and wet bonding modes achieved a bonding strengthen which was not apparently different from that of the control group. FIG. 3B was a transmission electron microscope image of mineralized dentin treated with 0.1M EDTA for 60 seconds or 25 mg/ml glycol chitosan-EDTA for 30 seconds. The EDTA group showed complete demineralization in a part of area and partial demineralization in some areas. The glycol chitosan-EDTA group showed partial demineralization of dentin, exhibiting obvious extrafibrillar spaces having no mineral and intact intrafibrillar mineralization.

FIGS. 4A and 4B compare the inhibitory effect of different concentrations of EDTA and EDTA cross-linked glycol chitosan (GCE) on the activity of endogenous recombinant human matrix metalloproteinase-9 (rHMMP-9), with 32% phosphoric acid (PA) as a control. In this experiment, the inhibitory effect of GCE on soluble MMP-9 was evaluated using purified recombinant human MMP-9 (rhMMP-9) and a generic MMP assay kit (Sensolyte, AnaSpec Inc., Fremont, CA, USA). The MMP assay kit contains an intact thiopeptolide that is cleaved by specific MMPs to release a sulfhydryl group that produces colored 2-nitro-5-thiobenzoic acid with Ellman's reagent. A series of EDTA and GCE solutions (50 mg/mL, 25 mg/mL, 10 mg/mL, 5 mg/mL, 1 mg/mL) were used as test agents and 32% $H_3PO_4$ was used for comparison. The thiopeptolide substrate solution was diluted to 0.2 mM with assay buffer in a 1:50 volume ratio. In the test compound groups, each well contained 2 µL of rhMMP-9 (19.6 ng/well), 10 µL of potential MMP inhibitor and 50 µL of thiopeptolide substrate solution. Additional assay buffer was added to generate 100 µL per well. The control groups included: (1) a positive control containing rhMMP-9 enzyme only without the potential anti-MMP agent; (2) an inhibitor control containing rhMMP-9 enzyme and 10 µL of GM6001, a known MMP inhibitor; (3) a test compound control containing assay buffer and test solutions at different concentrations; (4) a substrate control containing assay buffer. Readings were taken after 60 min of incubation at 37° C. Absorbance was measured at 412 nm using a 96-well plate reader (VICTOR Nivo™, PerkinElmer). Background absorbance was determined from the "substrate control" wells and subtracted from the readings of the other wells containing the thiopeptolide substrate. The potency of rhMMP-9 inhibition by GM6001, the kit-included MMP inhibitor, and the three concentrations of EDTA or GCE were expressed as percentages of the adjusted absorbance of the "positive control". Inhibition of MMP (%) was calculated as $1-([A]_{test\ compound\ group}-[A]_{test\ compound\ control})/([A]_{positive\ control}-[A]_{substrate\ control})$, where [A] represents the absorbance values of the wells. For each test solution, the mean absorbance value was calculated from values derived from six wells. FIG. 4A shows that EDTA and glycol chitosan-EDTA have similar inhibitory effects on the activity of endogenous recombinant human matrix metalloproteinase-9. FIG. 4B compares degree of degradation of dentin collagen in each group of the dentin mixed layers. The results showed that the degradation rate of collagen in the 32% phosphate group was the highest, followed by EDTA, and the EDTA crosslinked glycol chitosan was the weakest. This indicated that the protection effect of EDTA crosslinked glycol chitosan group on dentin collagen is the best.

FIGS. 5A and 5B show the cytotoxicity test of different dentin demineralizing agents 32% phosphoric acid (PA), 0.1M EDTA, or 25 mg/ml EDTA cross-linked glycol chitosan (GCE) with PBS as a control. FIG. 5A detects the mitochondrial dehydrogenase activity (Mito.) of human dental pulp stem cells (hDPSCs) that had been exposed to different dentin demineralizing agents. FIG. 5B detects intracellular DNA content of human dental pulp stem cells that had been exposed to different dentin demineralizing agents. The results showed that the cell viability was highest in the EDTA cross-linked glycol chitosan group, followed by the EDTA group, and the lowest in the 32% phosphate group, indicating that EDTA cross-linked glycol chitosan among the three dentin demineralizing agents had the lowest cytotoxicity.

Table 1 showed the characterization of molecular weight of glycol chitosan and EDTA cross-linked glycol chitosan by gel permeation chromatography, and the characterization of cross-linking degree between glycol chitosan and EDTA. The results showed that the molecular weight of glycol chitosan-EDTA formed after cross-linking was significantly increased, while the amount of free amino groups was significantly reduced, indicating that almost all of the amino groups on the glycol chitosan backbone and the carboxyl groups on the EDTA molecules reacted and covalently bonded to form amide bonds.

TABLE 1

| | Remaining free amino groups (%) | Parameters | | | |
|---|---|---|---|---|---|
| | | Mn (kDa) | Mw (kDa) | Mp (kDa) | PDI |
| Glycol chitosan | 100 | 56.39 | 122.49 | 81.38 | 2.17 |
| Glycol chitosan-EDTA | 4.3 ± 0.3 | 158.84 | 496.20 | 227.04 | 3.12 |

Abbreviations. Mn: number-average molecular weight; Mw: weight-average molecular weight; Mp: peak molecular weight; PDI: polydispersity index (Mw/Mn)

Example 3

This Example differed from Example 2 in:
(1) dissolving carboxymethyl chitosan in deionized water to form a chitosan solution at a concentration of 7 mg/ml;
(2) dissolving EDTA in deionized water to form an aqueous EDTA solution at a concentration of 200 mg/ml, mixing the aqueous EDTA solution with the carboxymethyl chitosan solution in an equal volume, adjusting the pH of the mixed solution to 6.0, dissolving the 1-ethyl-3-(3-dimethylaminopropyl)-carbodiimide cross-linking agent in the above-mentioned mixed solution at a concentration of 13 mg/ml, and continuously stirring for 12 hours at room temperature.

Example 4

This Example differed from Example 2 in:
(1) dissolving hyaluronic acid-like chitosan in deionized water to form a chitosan solution at a concentration of 8 mg/ml;
(2) dissolving EDTA in deionized water to form a 250 mg/ml aqueous EDTA solution, mixing the aqueous EDTA solution with the hyaluronic acid-like chitosan solution in an equal volume, dissolving the 1-ethyl-3-(3-dimethylaminopropyl)-carbodiimide cross-linking agent in the mixed solution at a concentration of 12 mg/ml, and continuously stirring for 13 hours at room temperature.

Example 5

This Example differed from Example 2 in:
(1) dissolving glycol chitosan in deionized water to form a chitosan solution at a concentration of 5 mg/ml;
(2) dissolving EDTA in deionized water to form an aqueous EDTA solution at a concentration of 100 mg/ml, mixing the aqueous EDTA solution with the glycol chitosan solution in an equal volume, adjusting the pH of the mixed solution to 6.0, dissolving the 1-ethyl-3-(3-dimethylaminopropyl)-carbodiimide cross-linking agent in the above-mentioned mixed solution at a concentration of 8 mg/ml, and continuously stirring for 15 hours at room temperature.

Example 6

This Example differed from Example 2 in:
(1) dissolving glycol chitosan in deionized water to form a chitosan solution at a concentration of 10 mg/ml; dissolving EDTA in deionized water to form an aqueous EDTA solution at a concentration of 300 mg/ml; and mixing the aqueous EDTA solution and the glycol chitosan solution in an equal volume; and
(2) dissolving the glutaraldehyde cross-linking agent in the above-mentioned mixed solution at a concentration of 0.8 mg/ml, and continuously stirring for 14 hours at room temperature.

Example 7

This Example differed from Example 2 in:
(1) dissolving glycol chitosan in deionized water to form a chitosan solution at a concentration of 10 mg/ml.
(2) dissolving EDTA in deionized water to form an aqueous EDTA solution at a concentration of 100 mg/ml, mixing the aqueous EDTA solution with the glycol chitosan solution in an equal volume, and dissolving 1-ethyl-3-(3-dimethylaminopropyl)-carbodiimide cross-linking agent in the above-mentioned mixed solution at a concentration of 15 mg/ml, and continuously stirring for 14 hours at room temperature.

The above contents are further detailed description of the present invention in combination with specific preferred embodiments, and cannot be considered as a limitation to the specific embodiments of the present invention. For those of ordinary skill in the technical field to which the present invention pertains, without departing from the premise of the inventive concept, a number of simple deductions or replacements can also be made, which should all be regarded as falling within the protection scopes of claims according to the present invention.

While the present invention has been particularly described, in conjunction with one or more specific embodiments, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:
1. A method of dental bonding restoration comprising:
providing a conjugate for dentin demineralization, the conjugate comprising an amide compound of a water-soluble chitosan and an aminocarboxylic acid metal chelating agent, the water-soluble chitosan is selected from the group consisting of glycol chitosan, carboxymethyl chitosan, chitosan hydrochloride, chitosan quaternary ammonium salt, chitosan sulfate ester, chitosan oligosaccharide or hyaluronic acid chitosan or a mixture thereof;
applying an effective amount of the conjugate to a tooth surface in need of restoration;
said conjugate demineralizing dentin collagen fibrils by selectively demineralizing and removing extrafibrillar minerals only at a bonding interface of the tooth surface while retaining intrafibrillar minerals; and
applying a dental bonding agent to the tooth surface, whereby the conjugate promotes penetration of the dental bonding agent into the dentin collagen fibrils by maintaining an original network structure of the dentin collagen fibrils during the selective demineralization step.
2. The method of claim 1 wherein the aminocarboxylic acid metal chelating agent is selected from the group consisting of ethylenediaminetetraacetic acid, hydroxyethyl ethylenediaminetriacetic acid, diethylenetriaminepentaacetic acid, aminotriacetic acid, dihydroxyethyl glycine, ethylene glycol tetraacetic acid, ethylenediamine diacetic acid, triethylenetetraaminehexaacetic acid, cyclohexanediamine tetraacetic acid, 1,4,7,10-tetraazacyclododecane-1,4,7,10-tetraacetic acid, and 1,4,8,11-tetraazacyclododecane-1,4,8,11-tetraacetic acid.

3. The method of claim 1 further including the step removing the conjugate prior to applying the dental bonding agent.

4. A method of dental bonding restoration comprising:
providing a conjugate for dentin demineralization, the conjugate comprising a chitosan glycol-EDTA conjugate formed using, as starting materials, 0.5-1 part by mass of a water-soluble cross-linked glycol chitosan, 10-30 parts by mass of ethylenediaminetetraacetic acid, and 0.8-1.5 parts by mass of a crosslinking agent;
applying an effective amount of the conjugate to a tooth surface in need of restoration;
said conjugate demineralizing dentin collagen fibrils by selectively demineralizing and removing extrafibrillar minerals only at a bonding interface of the tooth surface while retaining intrafibrillar minerals; and
applying a dental bonding agent to the tooth surface, whereby the conjugate promotes penetration of the dental bonding agent into the dentin collagen fibrils by maintaining an original network structure of the dentin collagen fibrils during the selective demineralization step.

5. The method of claim 4 wherein the water-soluble cross-linked glycol chitosan comprises a calcium chelator EDTA cross-linked glycol chitosan.

6. The method of claim 5 wherein the calcium chelator EDTA cross-linked glycol chitosan chelates calcium ions and reacts with minerals outside the dentin collagen fibrils to rapidly demineralize the tooth surface in a dental bonding restoration treatment within an acceptable clinical treatment time frame.

7. The method of claim 4 wherein the cross-linking agent is selected from the group consisting of 1-ethyl-3-(3-dim ethyl aminopropyl)-carbodiimide, N-hydroxysuccinimide, glutaraldehyde, bisimidate ester, maleimide, and mixtures thereof.

8. The method of claim 4 wherein the conjugate prevents and treats dental caries, and improves stability of the bonding interface to prolong a service life of the bonding restoration.

9. The method of claim 4 wherein the applied conjugate chelates calcium ion, reacts with minerals outside of dentin collagen fibrils, and completes demineralization within 30 seconds or less for acceptable clinical treatment.

10. The method of claim 4 wherein the pH value of the conjugate is pH 7-10.

11. The method of claim 4 wherein the conjugate comprises a dental demineralizing composition and further includes an orally acceptable excipient or vehicle.

12. The method of claim 4 wherein the conjugate comprises a dental bonding and restorative kit and further includes a dental bonding agent and/or restorative agent.

13. The method of claim 4 wherein the conjugate has;
a Mn greater than 40 kDa,
a Mw greater than 100 kDa,
a Mp greater than 70 kDa, and
a polydispersity index between 1 to 5.

14. The method of claim 4 wherein the conjugate has;
a Mn between 60 kDa to 600 kDa,
a Mw between 200 kDa to 800 kDa,
a Mp between 80 kDa to 600 kDa, and
a polydispersity index between 2 to 4.

15. A method of dental bonding restoration comprising:
providing a conjugate for dentin demineralization, the conjugate comprising a water-soluble calcium chelator EDTA cross-linked glycol chitosan, wherein the conjugate is composed of 0.5-1 part by mass of water-soluble glycol chitosan, 10-30 parts by mass of a calcium ion chelator ethylenediaminetetraacetic acid (EDTA), and 0.8-1.5 parts by mass of a crosslinking agent, the cross-linking agent is selected from the group consisting of 1-ethyl-3-(3-dimethylaminopropyl)-carbodiimide, N-hydroxysuccinimide, glutaraldehyde, bisimidate ester, maleimide, and mixtures thereof;
applying an effective amount of the conjugate to a tooth surface in need of restoration;
said conjugate demineralizing dentin collagen fibrils by selectively demineralizing and removing extrafibrillar minerals only at a bonding interface of the tooth surface while retaining intrafibrillar minerals, wherein the applied conjugate chelates at least calcium ions, reacts with minerals outside of dentin collagen fibrils, and rapidly demineralize the tooth surface in a dental bonding restoration treatment within an acceptable clinical treatment time frame; and
applying a dental bonding agent to the tooth surface, whereby the conjugate improves stability of the bonding interface to prolong a service life of the bonding restoration.

16. The method of claim 15 wherein the water-soluable calcium chelator EDTA cross-linked glycol chitosan chelates metal atoms or ions selected from the group consisting of calcium, magnesium, iron, copper, and zinc.

17. The method of claim 4 wherein content of free amino group of the conjugate is less than 15% as compared to the chelating agent of water-soluble cross-linked glycol chitosan prior to the conjugation reaction.

18. A method of dental bonding restoration comprising:
preparing a conjugate for dentin demineralization comprising;
mixing an aqueous water-soluble chitosan solution with an aqueous EDTA chelating agent solution to render a mixed solution;
dissolving a cross-linking agent in the mixed solution for reaction at room temperature;
rendering a chitosan glycol-EDTA conjugate of the water-soluble chitosan and the EDTA chelating agent solution, wherein the chitosan glycol-EDTA conjugate comprises 0.5-1 part by mass of the water-soluble chitosan, 10-30 parts by mass of the EDTA, and 0.8-1.5 parts by mass of the cross-linking agent;
applying an effective amount of the conjugate to a tooth surface in need of restoration;
said conjugate demineralizing dentin collagen fibrils by selectively demineralizing and removing extrafibrillar minerals only at a bonding interface of the tooth surface while retaining intrafibrillar minerals, wherein the applied conjugate chelates at least calcium ions, reacts with minerals outside of dentin collagen fibrils, and rapidly demineralize the tooth surface in a dental bonding restoration treatment within an acceptable clinical treatment time frame; and
applying a dental bonding agent to the tooth surface, whereby the conjugate improves stability of the bonding interface to prolong a service life of the bonding restoration.

19. The method of claim 18 further comprising in preparing the conjugate the steps of:

mixing the aqueous water-soluble chitosan solution at a concentration of 5 to 10 mg/ml with the aqueous EDTA solution at a concentration of 100 to 300 mg/ml in an equal volume,
adjusting a pH of the mixed solution to pH 6.0,
adding the cross-linking agent at a concentration of 8 to 15 mg/ml,
reacting for 12-16 hours at room temperature,
removing the unreacted residue via dialysis, and
freeze-drying to provide the conjugate for demineralizing dentin collagen fibril.

* * * * *